United States Patent [19]

Reed et al.

[11] Patent Number: 4,753,107
[45] Date of Patent: Jun. 28, 1988

[54] CORE HOLDER

[76] Inventors: Ross E. Reed, 36 O'Connor Dr.; H. Dean Williams, 32 O'Connor Dr., both of Splendora, Tex. 77372; Jess R. Needham, 18534 Woodland Hills, Humble, Tex. 77338

[21] Appl. No.: 837,951

[22] Filed: Mar. 10, 1986

[51] Int. Cl.⁴ ............................................ G01N 15/08
[52] U.S. Cl. ...................................................... 73/38
[58] Field of Search ..................... 73/38, 153; 166/250; 175/40, 50

[56] References Cited

U.S. PATENT DOCUMENTS

| | | | |
|---|---|---|---|
| 2,618,151 | 11/1952 | Leas | 73/38 |
| 2,705,418 | 4/1955 | Reichartz et al. | 73/38 |
| 2,737,804 | 3/1956 | Herzog et al. | 73/38 |
| 2,842,958 | 7/1958 | Sayre, Jr. et al. | 73/38 |
| 3,139,747 | 7/1964 | Ferrell et al. | 73/38 |
| 3,162,037 | 12/1964 | Hurst | 73/38 |
| 3,839,899 | 10/1974 | McMillen | 73/38 |
| 4,253,327 | 3/1981 | Wiley | 73/38 |
| 4,487,056 | 12/1984 | Wiley | 73/38 |
| 4,555,934 | 12/1985 | Freeman et al. | 73/38 |
| 4,573,342 | 3/1986 | Jones | 73/38 |
| 4,599,891 | 7/1986 | Braver et al. | 73/38 |

FOREIGN PATENT DOCUMENTS 0794434 1/1981 U.S.S.R. .............................. 73/38

OTHER PUBLICATIONS

RCH Series Care Holders, Product Description, Temco, Inc.
HCH and DCH Series Care Holders, Product Description, Temco, Inc.
HIP Reactors, Clover Leaf Quick Opening Closure, Product Description, High Pressure Equipment Company, Inc.

Primary Examiner—Stewart J. Levy
Assistant Examiner—Robert R. Raevis
Attorney, Agent, or Firm—Vaden, Eickenroht, Thompson & Boulware

[57] ABSTRACT

A core holder for use in the testing of a geologic core sample or other similiar cylindrical sample. An elastic rubber sleeve for receipt of a core sample is disposed in an open-ended, cylindrical cavity of an open-ended, cylindrical body. The ends of the sleeve are fitted over flanged ferrules. A cylindrical end plug is releasably locked in one end of the body with one of its ends inserted through the adjacent ferrule engage one end of the core sample. A cylindrical piston housing having a cylindrical cavity is releasably locked in the other end of the body. A cylindrical piston is disposed in the cavity of the piston housing with one of its ends protruding from an open end of the cavity and inserted through the adjacent ferrule to engage the other end of the core sample. Pressurized fluid moves the piston to apply axial force to the core sample. The sleeve is compressed by pressurized fluid to apply radial force to the core sample. Test fluid conduits are provided in the piston and the end plug.

1 Claim, 1 Drawing Sheet

CORE HOLDER

BACKGROUND OF THE INVENTION

This invention relates generally to core holders for use in the measuring of certain characteristics and the testing of the effect of various fluids on cores of geological formations of the earth or other similar cylindrical porous samples at pressures greater than atmospheric pressure and temperatures equal to or greater than room temperature, and, more particularly, to such a core holder with means for simultaneously subjecting such a sample to axial and radial pressures of unequal magnitude and the capability of being contained in a conventional laboratory oven during testing to simulate in situ conditions of the formation from which the core was taken.

It is common practice in the petroleum industry to remove core samples from subsurface geologic formations for testing. Typically, a core barrel is used to remove cores at intervals as a well is drilled. Some core samples are used for routine tests of the porosity, permeability and other important characteristics of a petroleum producing formation. Other core samples are used for waterflooding, enhanced recovery, formation damage or other special tests.

It is usually desirable for both routine and special tests of core samples to be conducted at pressures simulating those encountered in the subsurface geologic formations from which the core samples were removed. Usually, such tests are conducted at room temperature. However, it is sometimes desirable for such tests to be conducted at temperatures greater than room temperature. Accordingly, it is desirable to have core holders which permit such tests to be conducted at various pressures within a range of pressures greater than atmospheric pressure and temperatures within a range of temperatures greater than room temperature.

It is desirable to have a core holder with means for simultaneously subjecting a core sample to axial and radial pressures of unequal magnitude which is capable of being contained in a conventional laboratory oven during testing. It is also desirable to have such a core holder which can accommodate a varying number of fluid supply lines, electrical wires and the like necessary for various routine and special tests. It is not believed that the prior art provides such a core holder.

SUMMARY OF THE INVENTION

The present invention provides a core holder with means for simultaneously subjecting a geologic core or other similar cylindrical porous sample to axial and radial pressures of unequal magnitude. The core holder of the present invention is capable of being contained in a conventional laboratory oven during testing.

The core holder of the present invention comprises an open-ended, cylindrical body having an open-ended, cylindrical cavity. An elastic rubber sleeve having its ends stretch fitted over flanged ferrules is disposed in the cavity. The flanges of the ferrules and suitable seals engage the interior wall of the body to form an annular section between that wall and the sleeve. The core is disposed in the sleeve during testing.

A cylindrical piston housing is releasably locked in one end of the body. The piston housing has an open end disposed adjacent to one of the ferrules in the cavity of the body. A annular piston is disposed in the cavity of the piston housing with one of its ends inserted through the adjacent ferrule to engage one end face of the core sample. The other end of the piston has a larger diameter portion which slideably engages the interior wall of the piston housing and divides the cavity of the piston housing into first and second annular sections.

A cylindrical end plug is releasably locked in the other end of the piston. The end plug has a portion thereof inserted through the other ferrule to engage the other end face of the core. A varying number of passageways are provided in the end plug to which conduits can be connected for transmission of test fluids to and from the core. A varying number of conduits for resistivity testing wires, strain guage wires and the like can also be provided.

Pressurized fluid enters the annular section in the cavity of the body through a port in the body and compresses the elastic rubber sleeve onto the side wall of the core to apply radial pressure to the core. Pressurized fluid enters the first annular section in the cavity of the piston housing through a port in the piston housing and moves the piston to apply axial pressure to the core. Air in the second annular section in the cavity of the piston housing is vented through a vent in the piston housing as the piston moves. If the ports are connected to different pressurized fluid supplies, the core can be subjected to axial and radial pressures of different magnitudes.

These and many other advantages, features and objects of the present invention will be apparent from the following brief description of drawings, description of the preferred embodiment and claims, and the accompanying drawing.

DETAILED DESCRIPTION OF THE PREFERRED EMBODIMENT

Figure 1:
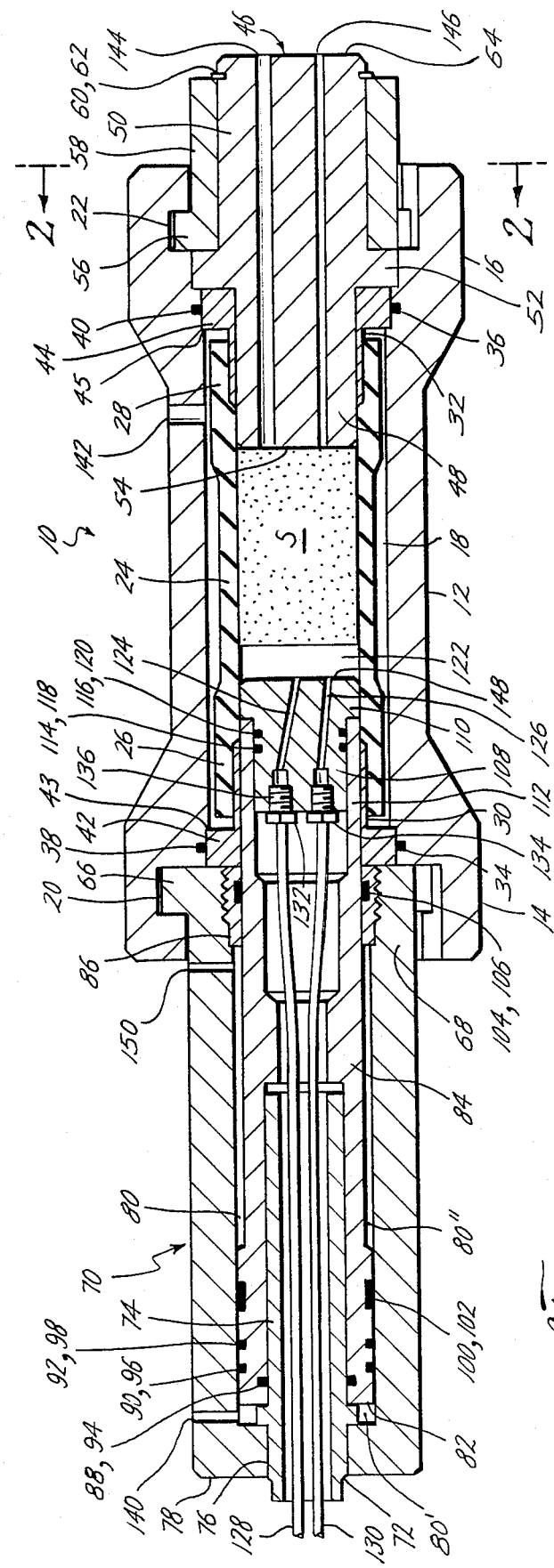
FIG. 1 is a longitudinal cross-sectional view of the core holder of the present invention.
Figure 2:
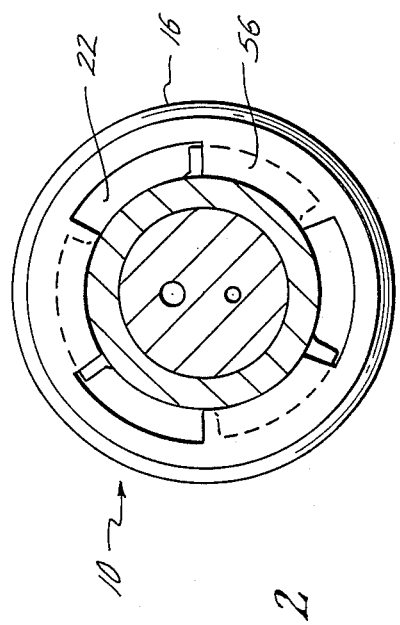
FIG. 2 is a cross-sectional view taken along lines 2—2 in FIG. 1.

The preferred embodiment of the core holder of the present invention is shown in FIGS. 1 and 2.

Core holder 10 comprises an open-ended, cylindrical body 12 having enlarged ends 14 and 16 and a concentric open-ended, cylindrical cavity 18. Grooves 20 and 22 adapted for receiving locking and releasing lugs are provided in the interior of enlarged ends 14 and 16. Elastic rubber sleeve 24 having its ends 26 and 28 stretch fitted over spaced apart ferrules 30 and 32 is provided to engage the side wall of cylindrical core sample S. During the use of core holder 10 for the testing of core S, sleeve 24, ferrules 30 and 32, and core S are concentrically disposed in cavity 18. As shown in FIG. 1, O-rings 34 and 36 fitted in circumferential grooves 38 and 40 in the interior wall of body 12 engage flanges 42 and 44 on ferrules 30 and 32 to seal cavity 18, and, thereby, form an annular section between the interior wall of body 12 and the exterior wall of sleeve 24. Alternatively, such grooves can be provided in flanges 42 and 44 on ferrules 30 and 32 and such O-rings fitted therein to engage the interior wall of body 12 to seal cavity 18, and, thereby, form an annular section between the interior wall of body 12 and the exterior wall of sleeve 24. Flanges 42 and 44 on ferrules 30 and 32 engage shoulders 43 and 45 in the interior wall of body 12 to retain sleeve 24 and ferrules 30 and 32 in position.

Cylindrical end plug 46 having a smaller diameter portion 48 and a larger diameter portion 50 separated by flange 52 is concentrically disposed in the interior of enlarged end 16 of body 12 with its smaller diameter portion 48 inserted through ferrule 32 such that its end face 54 engages one end face of core S and functions as a platen for receipt of axial pressure. Locking and releasing lugs 56 are provided on collar 58 rotatably mounted on the larger diameter portion 50 of end plug 46 to engage grooves 22 in the interior of enlarged end 16 of body 12, and, thereby, lock end plug 46 in position as shown in FIGS. 1 and 2. Flange 52 and retaining ring 60 fitted in circumferential groove 62 near end 64 of the larger diameter portion 50 of end plug 46 retain collar 58 on the larger diameter portion 50 of end plug 46 when lugs 56 are released from grooves 22 and end plug 46 is removed from the interior of enlarged end 16 of body 12.

Locking and releasing lugs 66 are provided on end 68 of open-ended, cylindrical piston housing 70 to engage grooves 20 in the interior of enlarged end 14 of body 12, and, thereby, lock piston housing 70 in position as shown in FIG. 1. End 72 of cylindrical piston sleeve 74 is forced fitted in cylindrical opening 76 through end 78 of piston housing 70 such that the remainder of piston sleeve 74 is concentrically disposed in cylindrical cavity 80 of piston housing 70 in the manner of a cantilever. End 82 of cylindrical, open-ended, hollow piston 84 is slideably mounted on piston sleeve 74 in cavity 80. Mounting ring 86 threadably fastened in the interior of end 68 of piston housing 70 supports piston 84 for sliding operation in cavity 80.

End 82 of piston 84 is of a larger diameter than the remainder of piston 84 and slideably engages the interior of piston housing 70. End 82 of piston 84 divides cavity 80 of piston housing 70 into a first annular section 80′ of variable length and a second annular section 80″ of variable length. The first annular section 80′ of cavity 80 is sealed by the force fit of end 72 of piston sleeve 74 in opening 76 through end 78 of piston housing 70, O-ring 88 fitted in circumferential groove 94 in the interior wall of end 82 of piston 84, O-rings 90 and 92 fitted in circumferential grooves 96 and 98 on the exterior of end 82 of piston 84, and flat sealing ring 100 fitted in circumferential groove 102 on the exterior of end 82 of piston 84. O-ring 88 engages the exterior of piston sleeve 74, and O-rings 90 and 92 and sealing ring 100 engage the interior of piston housing 70. The second annular section 80″ is sealed by O-rings 88, 90 and 92, sealing ring 100, and sealing ring 104. Flat sealing ring 104 is fitted in circumferential groove 106 in the interior wall of mounting ring 86 and engages the exterior of piston 84.

The smaller diameter portion 108 of cylindrical piston tip 110 is fitted in the interior of end 112 of piston 84. O-rings 114 and 116 fitted in circumferential grooves 118 and 120 on the smaller diameter portion 108 of piston tip 110 engage the interior wall of piston 84 to seal the core sample chamber 122 circumscribed by piston tip 110, end plug 46 and elastic rubber sleeve 24. Conduits 124 and 126 are provided in the interior of piston tip 110 for transmission of test fluids from supply lines 128 and 130 axially disposed in the interior of piston sleeve 74 and the interior of piston 84 to core sample chamber 122. Couplings 132 and 134 on supply lines 128 and 130 are threaded into inlet ports 136 and 138 of piston tip 110 to connect conduits 124 and 126 and supply lines 128 and 130. While two conduits 124 and 126 and two supply lines 128 and 130 are shown in FIG. 1, any number of such conduits which can be provided in the interior of piston tip 110 without reducing its strength below the minimum level necessary for operation of piston 84 and any number of such supply lines which can be provided in the interior of piston sleeve 74 and the interior of piston 84 without interfering with the sliding operation of piston 84 can be used with core holder 10. Conduits for resistivity testing wires, strain gauge wires and the like connected to core S can also be provided in the interior of piston tip 110 and such wires can be axially disposed in the interior of piston sleeve 74 and the interior of piston 84.

Prior to the use of core holder 10, core S is inserted in core chamber 122. Normally, this is accomplished with sleeve 24 and ferrules 30 and 32 disposed in cavity 18 of body 12 and piston housing 70 locked in position as shown in FIG. 1. After core S is so inserted, end plug 46 is locked in position as shown in FIGS. 1 and 2. Either before or after core S is so inserted, supply lines 128 and 130 are connected to a test fluid supply. A pressurized fluid supply is connected to annulus port 140 of piston housing 70 and the same or a different pressurized fluid supply is connected to annulus port 142 of body 12. If annulus port 140 and annulus port 142 are connected to different pressurized fluid supplies, it will be possible to subject core S to axial and radial pressures of unequal magnitude during testing. Conduits 144 and 146 in the interior of end plug 46 for transmission of test fluids away from core sample S are connected to suitable test fluid outlet lines. Finally, if desired, core holder 10 can be placed in a conventional laboratory oven for testing of core S at temperatures above room temperature.

During the use of core holder 10 for the testing of core S, pressurized fluid enters first annular section 80′ in piston housing 70 through port 140 and moves piston 84 forward such that the end face 148 of piston tip 110 engages one end face of core S to apply the desired axial pressure. Air in second annular section 80″ in piston housing 70 is vented through vent 150 as piston 84 moves forward. Pressurized fluid enters cavity 18 in body 12 through port 142 and compresses sleeve 24 onto the side all of core S to apply the desired radial pressure. Finally, test fluid enters core chamber 122 through conduits 124 and 126 in piston tip 110, passes through the open pores of core S, and exits core chamber 122 through conduits 144 and 146 in end plug 46.

While the present invention has been described and shown in connection with its preferred embodiment, it should be understood that there may be other embodiments which fall within the scope and spirit of the invention as defined by the following claims.

We claim:

1. A core holder for testing the porosity of a core of a geological formation of the earth or other porous material comprising: a hollow housing, a resilient sleeve within the housing to receive a core, means for supplying the outside of the sleeve with fluid under pressure to exert a radial compressive force on the core, first means closing one end of the housing, second means closing the other end of the housing, said second end closing means including an outer cylinder, a piston having a cylindrical opening therethrough located in the cylinder with one end extending into the sleeve, a replaceable end plug closing the end of the piston that extends into the sleeve, said plug having an end surface with an area equal to the cross-sectional area of the core for engaging the end of the core adjacent the plug, an inner cylinder positioned in the cylindrical opening of the piston to form with the outer cylinder an annular space to which fluid under pressure can be supplied to move the piston and the end plug into the housing to cause the end plug to exert a longitudinal compressive force thereon on the core, said core holder being further provided with a plurality of test fluid injection lines that extend through the inner cylinder and the end plug to supply fluid under pressure to the end of the core, and passages extending through the first end closing means to allow fluid passing through the core to flow out of the core holder.

* * * * *